United States Patent [19]
Lattner et al.

[11] Patent Number: 5,998,683
[45] Date of Patent: Dec. 7, 1999

[54] PROCESS FOR FORMING CYCLOPENTANE FROM DICYCLOPENTADIENE

[75] Inventors: James R. Lattner, Seabrook; C. Harry McMullen, Kingwood; Leonel E. Sanchez, League City; Steven E. Silverberg, Seabrook; Tronze-I Dennis Wu, Humble, all of Tex.

[73] Assignee: Exxon Chemicals Patents Inc., Houston, Tex.

[21] Appl. No.: 08/899,544

[22] Filed: Jul. 24, 1997

Related U.S. Application Data

[60] Provisional application No. 60/024,031, Aug. 6, 1996.

[51] Int. Cl.$^6$ ............... C07C 4/02; C07C 5/03; C07C 13/10; C07C 4/22
[52] U.S. Cl. ............ 585/317; 585/256; 585/259; 585/265; 585/20
[58] Field of Search ................ 585/317, 752, 585/20, 256, 259, 265

[56] References Cited

U.S. PATENT DOCUMENTS

| | | |
|---|---|---|
| 2,407,214 | 9/1946 | Birch et al. . |
| 2,420,030 | 5/1947 | Brandon . |
| 2,887,517 | 5/1959 | Noeske et al. . |
| 3,598,877 | 8/1971 | Fountain et al. . |
| 3,763,254 | 10/1973 | Engelhard et al. . |
| 3,998,897 | 12/1976 | Kovach et al. . |
| 4,048,242 | 9/1977 | Lauer et al. . |
| 4,721,823 | 1/1988 | Venier et al. ............... 585/20 |
| 4,929,782 | 5/1990 | Venier et al. ............... 585/375 |
| 5,096,933 | 3/1992 | Volkert . |
| 5,401,891 | 3/1995 | Keenan et al. . |

FOREIGN PATENT DOCUMENTS

| | | |
|---|---|---|
| 2 271 575 | 4/1994 | United Kingdom . |
| 2 273 107 | 6/1994 | United Kingdom . |

*Primary Examiner*—Walter D. Griffin
*Attorney, Agent, or Firm*—Andrew B. Griffis; Douglas J. Collins

[57] ABSTRACT

A method for producing a cyclopentane product which comprises the following steps: (a) cracking dicyclopentadiene to form a cyclopentadiene-rich stream and a higher boiling liquids stream; (b) separating the cyclopentadiene-rich stream from the higher boiling liquids stream; (c) diluting the cyclopentadiene-rich stream with recycled saturates such that the cyclopentadiene content is limited to between about 5–50%; (d) conducting a first hydrogenation of the cyclopentadiene-rich stream in the presence of hydrogen and a first catalyst, and at a temperature (i.e., preferably between about 26 to 94° C., more preferably in the range between about 37 to 66° C.) which is capable of avoiding the repolymerization of cyclopentadiene to dicyclopentadiene, thereby forming a cyclopentadiene-depleted stream; (e) conducting a second hydrogenation of the cyclopentadiene-depleted stream in the presence of a second catalyst wherein any residual olefins and/or cyclopentadiene contained within the cyclopentadiene-depleted stream are saturated, thereby forming a crude cyclopentane product; and (f) flash stripping the crude cyclopentane product to form the cyclopentane product comprising about 95% pure cyclopentane.

18 Claims, 1 Drawing Sheet

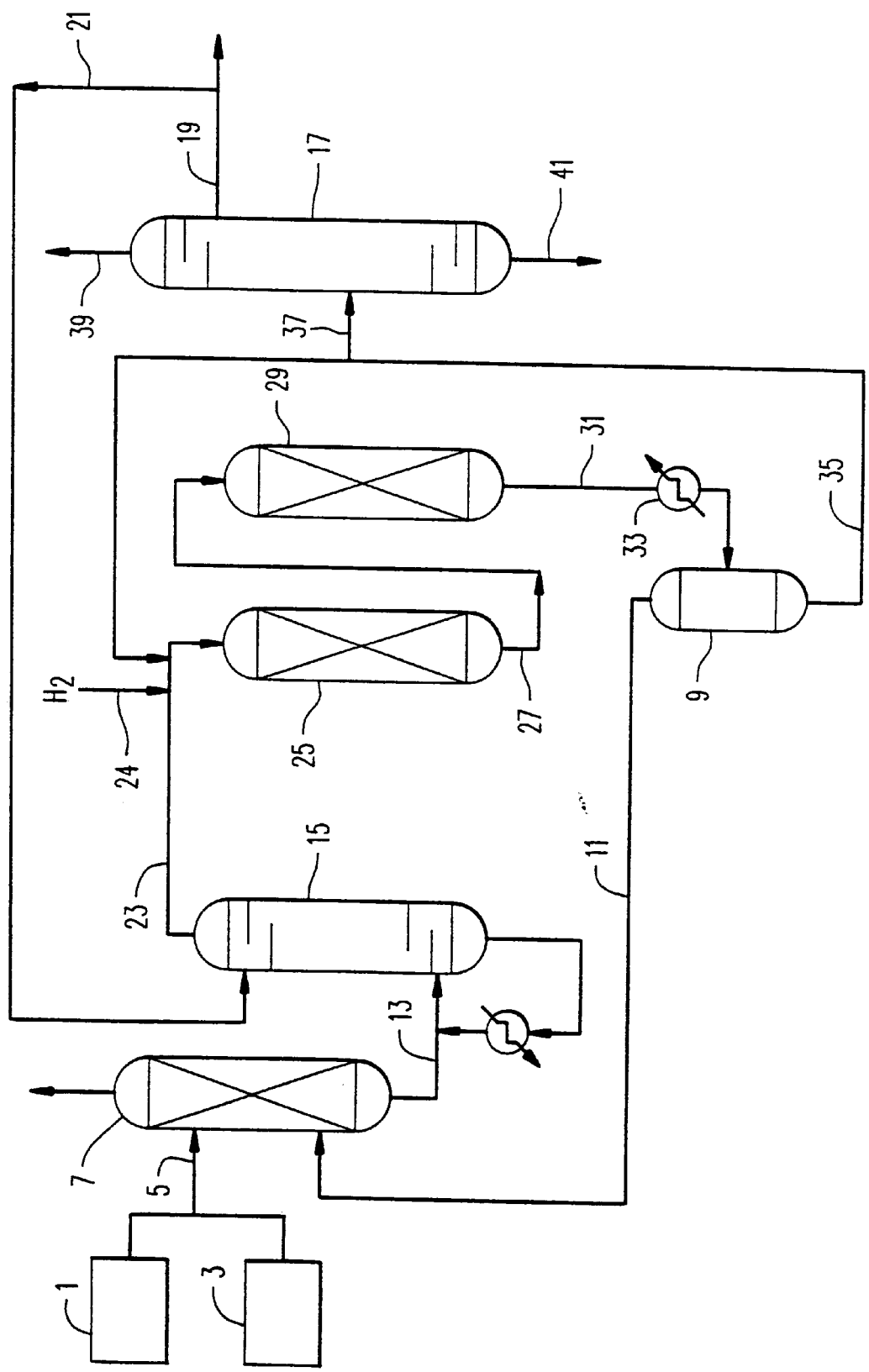

PROCESS FOR FORMING CYCLOPENTANE FROM DICYCLOPENTADIENE

This is a formal U.S. patent application based upon U.S. Provisional Patent Application, Ser. No. 60/024,031, filed Aug. 6, 1996.

The present invention is generally directed to a novel process for recovering high-purity cyclopentane or methylcyclopentane from commercially available dicyclopentadiene or dimethyldicyclopenadiene, respectively. In particular, this process involves the splitting or decomposition of dicyclopentadiene to cyclopentadiene, followed by the hydrogenation of cyclopentadiene directly to cyclopentane.

BACKGROUND OF THE INVENTION

Cellular organic rigid thermosetting plastic foams used for thermal insulation are well know in the art. Such foams can be made with urethane linkages, or made with a combination of both isocyanurate linkages and urethane linkages, or they can be made via the well known condensation reaction of formaldehyde with phenol, urea, and melamine. All such plastic foams must utilize an expansion agent, often referred to as a "blowing agent."

The prior art is replete with references to techniques of expanding foam cells. For many years, the dominant blowing agent for all thermosetting foams was trichloromonofluoromethane (CFC-11). Hydrogenated chlorofluorocarbons (HCFC's) are considered to be environmentally friendly expansion agents, but still contain some chlorine, and therefore have an "Ozone Depletion Potential" (ODP). Because of the ODP, the HCFC's have been mandated for eventual phase-out.

Hydrocarbon blowing agents are also known, which class includes halogen-free and $CO_2$-free blowing agents. For example, U.S. Pat. No. 5,182,309 (Hutzen) teaches the use of iso- and normal-pentane in various emulsion mixtures. Another example of hydrocarbon blowing agents is taught in U.S. Pat. No. 5,096,933 (Volkert), pointing out the virtues of commercial cyclopentane distilled and extracted from natural gas wells.

Accordingly, cyclopentane is expected to replace ozone-depleting halogen-containing compounds as the blowing agent for manufacturing of polyurethane foam insulation. The volatility and low thermal conductivity of cyclopentane make it uniquely suitable for this application.

One route for manufacturing cyclopentane involves recovery by distillation from naphtha streams derived from crude oil or field natural gasoline. Very limited quantities of cyclopentane can be produced via this route due to the low concentrations of naturally occurring cyclopentane. Furthermore, cyclopentane product purity via this route is limited to approximately 75% by the presence of 2,2-dimethyl butane (which has a boiling point less than 1° F. (0.55° C.) different from cyclopentane). Further purification requires more expensive processing such as extractive distillation.

Extracted cyclopentane has at least five problems which heretofore virtually prohibited it from being considered a serious candidate as a commercial blowing agent for rigid foam insulation. The first problem is that its limited supply is considerably below the amount needed to meet the quantity demanded of a commercial compound. The second problem is that this inadequate supply contains at least twenty-two percent impurities in the form of hexane isomers and n-pentane, which impurities significantly reduce insulating value of foam made therefrom. The third problem is that extracted cyclopentane is not miscible with the common polyester polyols which are used with HCFC'S, nor those that were used with CFC-11. The fourth problem is that extracted cyclopentane does not reduce the viscosity of the polyester polyol foamable blend to a workable level, even when liquid fire retardants are utilized.

The fifth problem is that the foam produced with extracted cyclopentane will not pass the ASTM E-84 maximum 75 Flame Spread Index even with moderate flame retardant.

Another possible route for manufacturing cyclopentane involves hydrogenation of cyclopentene; however, cyclopentene is not readily available in commercial quantities.

Another route to produce a high purity cyclopentane, and the subject of the present invention, involves splitting dicyclopentadiene (DCPD) into cyclopentadiene (CPD) monomer and hydrogenating the monomer to form cyclopentane. A key advantage of this route is an abundance of commercially available, low-cost DCPD raw material. Technical obstacles involve: (1) effective splitting of DCPD without forming heavy resins that diminish product yields and foul the splitting equipment; and (2) preventing unwanted reaction of the highly reactive monomer which decreases desired product yield, form unwanted by-products, and can lead to deactivation of the hydrotreating catalyst. Examples of such processes are set forth in GB-A-2271575 and GB-A-2273107, which are incorporated herein by reference and which are commonly assigned to the assignee of the present invention.

The present invention also provides many additional advantages which shall become apparent as described below.

SUMMARY OF THE INVENTION

A method for producing a cyclopentane product which comprises the following steps: (a) cracking dicyclopentadiene to form a cyclopentadiene-rich stream and a higher boiling liquids stream; (b) separating the cyclopentadiene-rich stream from the higher boiling liquids stream; (c) diluting the cyclopentadiene-rich stream with recycled saturates such that the cyclopentadiene content is limited to between about 5–50%; (d) conducting a first hydrogenation of the cyclopentadiene-rich stream in the presence of hydrogen and a first catalyst, and at a temperature (i.e., preferably between about 26 to 94° C., more preferably in the range between about 37 to 66° C.) which is capable of avoiding the repolymerization of cyclopentadiene to dicyclopentadiene, thereby forming a cyclopentadiene-depleted stream; (e) conducting a second hydrogenation of the cyclopentadiene-depleted stream in the presence of a second catalyst wherein any residual olefins and/or cyclopentadiene contained within the cyclopentadiene-depleted stream are saturated, thereby forming a crude cyclopentane product; and (f) flash stripping the crude cyclopentane product to form the cyclopentane product comprising about 95% pure cyclopentane.

Optionally, separating hydrogen from the crude cyclopentane product of step (e) prior to flash stripping step (f). The hydrogen which is separated from the crude cyclopentane product of step (e) may be further processed to recover any cyclopentane remaining in the vapor phase.

The first hydrogenation catalyst is at least one catalyst selected from the group consisting of: palladium-on-alumina or other supported Group VIII transition metal catalysts which are active at temperatures low enough to avoid repolymerization of the cyclopentadiene.

The second hydrogenation catalyst is at least one catalyst selected from the group consisting of: massive nickel, nickel molybdenum, cobalt molybdenum and and other conventional hydrotreating catalysts active for olefin saturation (e.g., any noble metal catalysts).

This process according to the present invention can also be used to manufacture methylcyclopentane from dimethyldicyclopentadiene.

Other and further objects, advantages and features of the present invention will be understood by reference to the following specification in conjunction with the annexed drawings, wherein like parts have been given like numbers.

BRIEF DESCRIPTION OF THE DRAWINGS

The FIGURE is a schematic diagram of the cyclopentane process according to the present invention.

DESCRIPTION OF THE PREFERRED EMBODIMENTS

A process for manufacturing high-purity (i.e., 95% or greater) cyclopentane by splitting dicyclopentadiene and completely hydrogenating the cyclopentadiene monomer in a single unit is illustrated in the attached FIGURE.

The general process scheme involves diluting commercially available dicyclopentadiene with an aliphatic or aromatic hydrocarbon fluid of specific volatility and solvency. This material is then introduced into a distillation apparatus in which the dicyclopentadiene decomposes (or depolymerizes) to cyclopentadiene monomers. Reflux to the distillation apparatus consists of a cyclopentane product recycle stream. This reflux aids distillation and dilutes the cyclopentadiene monomer to prevent re-dimerization and cyclopentadiene yield reduction. The overhead stream from this step is a stream containing cyclopentane and cyclopentadiene.

This stream is further diluted with cyclopentane-rich recycle liquid obtained from the high-pressure separator drum. The purpose of the dilution is to minimize cyclopentadiene dimerization and to allow controlling of the exotherm in the subsequent hydrotreating reactors.

The cyclopentadiene/cyclopentane stream is then pumped to a reactor and combined with a stoichiometric excess of hydrogen contained in a treatgas stream. It is then passed over a palladium-on-alumina catalyst where the bulk of the hydrogenation reaction occurs converting most of the cyclopentadiene to cyclopentane. The first reactor effluent flows to a second reactor containing a massive nickel catalyst where any remaining olefins (i.e., cyclopentene) are saturated.

The fully hydrogenated nickel reactor effluent is cooled and enters a high-pressure flash drum. The vapor from this drum, which contains primarily hydrogen but also contains some cyclopentane vapor, is contacted with the dicyclopentadiene feed stream in an absorber tower to minimize cyclopentane losses.

A portion of the liquid product from the high-pressure separator drum is recycled as described earlier. The remainder flows to a product stripping tower in which any remaining dissolved hydrogen and any compounds heavier than cyclopentane are removed. The stripper bottoms may be recycled to the dicyclopentadiene cracking tower.

The process according to the present invention can best be described by referring to the FIGURE, wherein DCPD and an aliphatic hydrocarbon fluid of specific solvency and volatility are fed from tanks 1 and 3, respectively, via conduit 5 to absorber tower 7. In tower 7, liquid from conduit 5 is contacted with a gas stream from conduit 11 containing primarily excess hydrogen along with some cyclopentane. The DCPD and diluent with dissolved cyclopentane is routed from tower 7 via conduit 13 to distillation tower 15. In distillation tower 15, DCPD decomposes to cyclopentadiene, the cyclopentadiene monomer is separated from less volatile substances and the monomer is diluted to between 5–50% to prevent re-dimerization and yield reduction. The liquid cyclopentadiene and cyclopentane mixture is taken as a liquid distillate from tower 15 via conduit 23 where it is further diluted with cyclopentane-rich recycle liquid obtained from product stripping tower 17 via conduits 19 and 21. The purpose of this dilution is to minimize cyclopentadiene dimerization and to allow controlling of the exotherm in the subsequent hydrotreating reactors. The cyclopentadiene/cyclopentane stream having a cyclopentadiene content of between about 5–50% is mixed with a stoichiometric excess of hydrogen from conduit 24. The combined hydrogen cyclopentadiene/cyclopentane stream is then sent to first hydrogenation reactor 25 wherein it is passed over a palladium-on-alumina catalyst where the bulk of the hydrogenation reaction occurs converting most of the cyclopentadiene to cyclopentane. The effluent from first hydrogenation reactor 25 is taken via conduit 27 and sent to the top of second hydrogenation reactor 29 containing a massive nickel catalyst where any remaining olefins (i.e., cyclopentene) are saturated.

The fully hydrogenated product stream is taken as liquid from the bottom of reactor 29 via conduit 31 and cooled via heat exchanger 33 and thereafter sent to high-pressure flash drum 9. The overhead (i.e., primarily hydrogen, but also containing some cyclopentane vapor) from flash drum 9 is returned to tower 7 via conduit 11, as discussed before, to minimize cyclopentane losses. The bottoms from flash drum 9 are taken via conduit 35 and either recycled to tower 15 via conduit 40 or sent via conduit 37 to product stripping tower 17 wherein any remaining dissolved hydrogen and any compounds lighter than cyclopentane are removed overhead via conduit 39. The bottoms from stripping tower 17 are removed via conduit 41 and, optionally, recycled to tower 15 or purged from the system. Cyclopentane product is recovered from an intermediate section of stripper tower 17 via conduit 19 and either sent to tankage, not shown, or recycled via conduit 21 upstream of the first hydrogenation reactor 25, as discussed above. The cyclopentane is preferably 95% pure cyclopentane at this point.

The aforementioned process can also be used to manufacture methylcyclopentane from dimethyldicyclopentadiene.

The unique cyclopentane product produced in accordance with the present invention is particularly useful in a method of producing a rigid thermosetting plastic foam described in co-pending and commonly assigned U.S. patent application, Ser. No. 08/389,955, filed Feb. 17, 1995, now abandoned, and U.S. patent application, Ser. No. 08/498,276, filed Jul. 3, 1995, now U.S. Pat. No. 5,578,652, which are incorporated herein by reference. The method of producing a rigid thermosetting plastic foam comprises the steps of: (1) preparing a first of two foam forming blends using polymeric polymethylene polyphenylisocyanate; (2) preparing a second of two foam forming blends by mixing together: (a) a polyol component comprised of a majority of polyester polyol, (b) a liquid flame retardant, (c) a suitable catalyst to promote the reaction between the first of two foam forming blends and the polyol component, and (d) a blowing agent comprised at least partially from depolymerization of dicyclopentadiene to yield cyclopentane according to the main feature of the present invention; and (3) mixing together the first and second foam forming blends to form the rigid thermosetting plastic foam.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

We claim:

1. A method for producing a cyclopentane product which comprises the following steps:
   (a) cracking dicyclopentadiene to form a cyclopentadiene-rich stream and a higher boiling liquids stream;
   (b) separating said cyclopentadiene-rich stream from said higher boiling liquids stream;
   (c) diluting said cyclopentadiene-rich stream with recycled saturates such that the cyclopentadiene content is limited to between about 5–50 weight %;
   (d) conducting a first hydrogenation of said cyclopentadiene-rich stream in the presence of hydrogen and a first catalyst, and at a temperature which is capable of avoiding the repolymerization of cyclopentadiene to dicyclopentadiene, thereby forming a cyclopentadiene-depleted stream;
   (e) conducting a second hydrogenation of said cyclopentadiene-depleted stream in the presence of a second catalyst wherein any residual olefins and/or cyclopentadiene contained within said cyclopentadiene-depleted stream are saturated, thereby forming a crude cyclopentane product; and
   (f) treating said crude cyclopentane product to form said cyclopentane product.

2. The method according to claim 1 wherein said treating step (f) is a flash stripping process.

3. The method according to claim 1 further comprising the step of separating hydrogen from said crude cyclopentane product of step (e) prior to treating step (f).

4. The method according to claim 1 wherein said cyclopentane product is at least 95 weight % pure cyclopentane.

5. The method according to claim 1 wherein said first catalyst is at least one catalyst selected from the group consisting of: palladium-on-alumina or other supported Group VIII transition metal catalysts which are active at temperatures sufficient to partially saturate cyclopentadiene while avoiding repolymerization of said cyclopentadiene.

6. The method according to claim 1 wherein said second catalyst is at least one catalyst selected from the group consisting of: massive nickel, nickel molybdenum, and cobalt molybdenum.

7. The method according to claim 1 wherein said temperature in first hydrogenation step (d) is in the range between about 26 to 94° C.

8. The method according to claim 7 wherein said temperature in first hydrogenation step (d) is in the range between about 37 to 66° C.

9. The method according to claim 3 wherein said hydrogen which is separated from said crude cyclopentane product of step (e) is further processed to avoid cyclopentane losses.

10. A method for producing a methylcyclopentane product which comprises the following steps:
    (a) cracking dimethyldicyclopentadiene to form a methylcyclopentadiene-rich stream and a higher boiling liquids stream;
    (b) separating said methylcyclopentadiene-rich stream from said higher boiling liquids stream;
    (c) diluting said methylcyclopentadiene-rich stream with recycled saturates such that the methylcyclopentadiene content is limited to between about 5–50 weight %;
    (d) conducting a first hydrogenation of said methylcyclopentadiene-rich stream in the presence of hydrogen and a first catalyst, and at a temperature which is capable of avoiding the repolymerization of methylcyclopentadiene to dimethyldicyclopentadiene, thereby forming a methylcyclopentadiene-depleted stream;
    (e) conducting a second hydrogenation of said methylcyclopentadiene-depleted stream in the presence of a second catalyst wherein any residual olefins and/or methylcyclopentadiene contained within said methylcyclopentadiene-depleted stream are saturated, thereby forming a crude methylcyclopentane product; and
    (f) treating said crude methylcyclopentane product to form said methylcyclopentane product.

11. The method according to claim 10 wherein said treating step (f) is a flash stripping process.

12. The method according to claim 10 further comprising the step of separating hydrogen from said crude methylcyclopentane product of step (e) prior to treating step (f).

13. The method according to claim 10 wherein said methylcyclopentane product is at least 95 weight % pure methylcyclopentane.

14. The method according to claim 10 wherein said first catalyst is at least one catalyst selected from the group consisting of: palladium-on-alumina or other supported Group VIII transition metal catalysts which are active at temperatures sufficient to partially saturate methylcyclopentadiene while avoiding re-polymerization of said methylcyclopentadiene.

15. The method according to claim 10 wherein said second catalyst is at least one catalyst selected from the group consisting of: massive nickel, nickel molybdenum, and cobalt molybdenum.

16. The method according to claim 10 wherein said temperature in first hydrogenation step (d) is in the range between about 26 to 94° C.

17. The method according to claim 16 wherein said temperature in first hydrogenation step (d) is in the range between about 37 to 66° C.

18. The method according to claim 12 wherein said hydrogen which is separated from said crude methylcyclopentane product of step (e) is further processed to avoid methylcyclopentane losses.

* * * * *